United States Patent [19]

Love

[11] Patent Number: 5,723,148
[45] Date of Patent: Mar. 3, 1998

[54] TOPICAL PHARMACEUTICAL COMPOSITIONS

[75] Inventor: William Guy Love, Horsham, England

[73] Assignee: Novartis Corp., Summit, N.J.

[21] Appl. No.: 583,255

[22] Filed: Jan. 5, 1996

[30] Foreign Application Priority Data

Jan. 5, 1995 [GB] United Kingdom .................... 9500116

[51] Int. Cl.$^6$ .................................................. A61K 9/127
[52] U.S. Cl. ............................................................ 424/450
[58] Field of Search .......................... 426/480; 514/185; 424/641, 450; 428/402.2

[56] References Cited

U.S. PATENT DOCUMENTS

| | | | |
|---|---|---|---|
| 4,708,861 | 11/1987 | Popesui | 424/1.1 |
| 5,064,655 | 11/1991 | Uster | 424/450 |
| 5,179,120 | 1/1993 | Vogel et al. | 514/410 |
| 5,270,053 | 12/1993 | Schneider et al. | 424/450 |

FOREIGN PATENT DOCUMENTS

| | | |
|---|---|---|
| 0633024 | 1/1995 | European Pat. Off. . |
| 9011064 | 10/1990 | WIPO . |
| 9505818 | 3/1995 | WIPO . |

OTHER PUBLICATIONS

Spikes, Photochemistry & Photobiology vol. 43, No. 6 pp. 691–699, 1986.

*Primary Examiner*—Gollamudi S. Kishore
*Attorney, Agent, or Firm*—Marla J. Mathias; Gregory D. Ferraro

[57] ABSTRACT

A topically administrable pharmaceutical composition comprising (A) zinc phthalocyanine, (B) as carrier for (A), (i) a monoalkyl ether of diethyleneglycol substantially in the absence of a N-alkylpyrrolidone, a N,N-dialkylbenzamide or dimethyl sulphoxide, or (ii) a mixture of a monoalkyl ether of diethyleneglycol with a lipid and (C) a gelling agent.

20 Claims, No Drawings

TOPICAL PHARMACEUTICAL COMPOSITIONS

This invention relates to topically administrable pharmaceutical compositions which are especially useful in the treatment of psoriasis.

The therapeutic use of zinc phthalocyanine complex in photodynamic chemotherapy for the treatment of turnouts is known. J. D. Spikes, Photochem. Photobiol, 43,691 (1986) describes the administration of zinc phthalocyanine complex intraperitoneally to mice or rats in vivo in the form of an aqueous suspension and the irradiation of the carcinoma induced in the animals with high energy light, preferably concentrated visible light from a laser.

The use of intraperitoneal administration in human therapy generally gives rise to problems because of the pain caused by piercing of the abdominal cavity and the great demands made on the skill of the physician. Attempts have therefore been made to find alternative parenteral dosage forms which are more acceptable to the patient but are also capable of ensuring systemic distribution of the zinc phthalocyanine complex. In U.S. Pat. No. 5,270,053 there are described intravenously administrable liposome dispersions comprising the zinc phthalocyanine complex and one or more synthetic phospholipids, particularly for use in the treatment of rumours.

It has been found that topical administration of the zinc phthalocyanine complex to human skin can result in penetration of the complex into the epidermis to facilitate the use of the complex in the treatment of hyperproliferative skin diseases such as psoriasis by photodynamic therapy in which irradiation of the treated skin kills the hyperproliferative basal cell layer. Topical application of the complex avoids the need to photosensitise the entire skin; the topical composition need be applied only to affected areas of the skin.

The formulation of topically administrable dosages of the zinc phthalocyanine complex has proved problematic, mixtures of the complex with many solubilising agents failing to show significant skin penetration. It has now been found, in accordance with the present invention, that by formulating the complex with certain selected carriers, a stable topically administrable gel can be produced which exhibits sufficient skin penetration for it to be used in the treatment of hyperproliferative diseases such as psoriasis by photodynamic therapy.

Accordingly, the present invention provides a topically administrable pharmaceutical composition comprising (A) zinc phthalocyanine, (B) as carrier for (A), (i) a monoalkyl ether of diethyleneglycol substantially in the absence of a N-alkylpyrrolidone, a N,N-dialkylbenzamide or dimethyl sulphoxide, or (ii) a mixture of a monoalkyl ether of diethyleneglycol with a lipid, and (C) a gelling agent.

The monoalkyl ether of diethyleneglycol is usually a $C_1$ to $C_4$ alkyl ether of this glycol, for example the methyl, ethyl, n-propyl, isopropyl or n-butyl ether of this glycol. An especially preferred monoalkyl ether is the ethyl ether of diethyleneglycol.

Where the carrier (B) is a mixture of a monoalkyl ether of diethyleneglycol with a lipid, the lipid is preferably a phospholipid, which may be a natural phospholipid such as egg phosphatidylcholine, soya bean phosphatidylcholine or beef brain sphingomyelin, a synthetic phospholipid, for example a synthetic phosphatidylcholine such as dimydstoyl phosphatidylcholine, dipalmitoyl phosphatidylcholine, distearoyl phosphatidylcholine, dioleoyl phosphatidylcholine, dilinoleoyl phosphatidylcholine, dilauryloyl phosphatidylcholine, 1-palmitoyl-2-oleoyl phosphatidylcholine, 1-myristoyl-2-palmitoyl phosphatidylcholine and 1-palmitoyl-2-myristoyl phosphatidylcholine, a synthetic phosphatidylglycerol such as dilauryloyl phosphatidylglycerol, dimyristoyl phosphatidylglycerol, dipalmitoyl phosphatidylglycerol and dioleoyl phosphatidylglycerol, a synthetic phosphatidic acid such as dimyristoyl phosphatidic acid and dipalmitoyl phosphatidic acid, a synthetic phosphatidylethanolamine such as dimyristoyl phosphatidylethanolime and dipalmitoyl phosphatidylethanolamine or a synthetic phosphatidylserine such as dimyristoyl phosphatidylserine, dipalmitoyl phosphatidylserine and dioleoyl phosphatidylserine, or a mixture of two or more thereof.

Preferred synthetic phospholipids include phosphatidylcholines and mixtures thereof with phosphatidylserines. Preferred natural phospholipids are natural phosphatidylcholines. In certain particularly preferred embodiments of the invention, the lipid is palmitoyl oleoyl phosphatidylcholine, soya bean phosphatidylcholine, or a mixture of palmitoyl oleoyl phosphatidylcholine and dioleoyl phosphatidylserine. Where the carrier (B) is a mixture of a monoalkyl ether of diethyleneglycol with a lipid, the lipid may be in the form of liposomes in which the zinc phthalocyanine complex is entrapped. The lipid component of the liposomes is usually a synthetic phospholipid such as hereinbefore described, preferably a mixture of a neutral synthetic phospholipid, particularly a synthetic phosphatidylcholine, with a charged synthetic phospholipid, particularly a phosphatidylserine.

In a preferred embodiment, the synthetic phospholipid component of the liposomes is a mixture of palmitoyl oleoyl phosphatidylcholine and dioleoyl phosphatidylserine. In liposomes comprising a mixture of a phosphatidylcholine and a phosphatidylserine, the weight ratio of phosphatidylcholine to phosphatidylserine is generally from 60:40 to 95:5, preferably from 70:30 to 90:10. The liposomes may be reconstituted from dehydrated liposomes, the dehydration having generally been effected by lyophilisation in the presence of a cryoprotectant such as lactose.

In compositions of the invention where the carrier (B) is a mixture of a monoalkyl ether of diethyleneglycol and a lipid, the lipid optionally being present in the form of liposomes, the lipid may be present generally in an amount of up to 1 g per ml of the monoalkyl ether, for example 0.01 g to 0.8 g, particularly 0.1 to 0.6 g, per ml of the monoalkyl ether.

The zinc phthalocyanine (A) is generally present in compositions of the invention in an amount of 1 to 500 µg, preferably 50 to 400 µg, per ml of the carrier (B).

The gelling agent (C) may be an organic gel-forming polymer. Because of their high compatibility with the carrier (B), cellulosic gel-forming polymers are preferred, including cellulose, alkylcelluloses such as methyl cellulose or ethyl cellulose, hydroxyalkyl celluloses such as hydroxyethyl cellulose or hydroxypropyl cellulose, or hydroxyalkyl alkyl celluloses such as hydroxypropyl ethyl cellulose. Hydroxyalkyl celluloses are particularly preferred, especially hydroxypropyl cellulose. The amount of gelling agent needed for a gel-forming composition can readily be determined by simple experiment. It is generally used in an amount of 0.1 to 10 parts by weight per 100 parts by volume of the composition.

The composition of the invention may also contain, as diluent, a polyoxyalkylene glycol such as a polyethylene glycol, usually having a molecular weight of 200 to 1000, preferably 300 to 500, in an amount up to 90% by volume of the composition. Other optional excipients include conventional additives such as antioxidants and preservatives.

A composition of the invention may be prepared by a process which comprises mixing a solution of (A) zinc phthalocyanine in a carrier (B) as hereinbefore defined with a gelling agent (C) and any optional excipients, heating if necessary, for example at 30°–80° C., to form a substantially homogeneous composition followed by cooling, until a gel is formed.

The solution of zinc phthalocyanine (A) in the carrier (B), where (B) contains lipid, can be prepared by dissolving the lipid in the monoalkyl ether of diethyleneglycol and dissolving (A) in the resulting solution, heating if necessary, for example at a temperature up to 80° C. The solution of (A) in (B) can alternatively be prepared by reconstituting dehydrated liposomes containing entrapped zinc phthalocyanine by mixing the dehydrated liposomes with the monoalkyl ether of diethyleneglycol. In a further alternative, the solution of (A) in (B) can be prepared by dissolving (A) together with a lipid in an organic solvent, removing solvent from the resulting solution to leave a residue and dissolving the residue in the monoalkyl ether of diethyleneglycol.

Liposomes containing entrapped zinc phthalocyanine can be prepared using known procedures. For example, liposomes comprising, as the lipid component, palmitoyl oleoyl phosphatidylcholine or a mixture thereof with dioleoyl phosphatidylcholine, can be prepared as described in U.S. Pat. No. 5,270,053. Conventional antioxidants such as tocopherols may be incorporated into the liposomes. The lipsomes may be dehydrated in a conventional manner, preferably by lyophilisation (freeze drying) in the presence of a cryoprotectant such as lactose.

A composition of the invention may be topically applied to an affected area of a patient's body to provide thereon a therapeutically effective amount of the zinc phthalocyanine complex. Thus a gel containing the complex may be applied to the affected area in a conventional manner, if desired after the skin has been washed to remove psoriasis scales. Penetration of the zinc phthalocyanine into the skin can be enhanced by placing an occlusion barrier over the affected area after application of the gel. In some instances, one application of the gel may suffice to obtain absorption of sufficient zinc phthalocyanine into the affected skin, while in other instances several applications may be needed. After allowing time for absorption of the zinc phthalocyanine, for example 1 to 24 hours, the affected area may be irradiated with visible radiation, preferably radiation having a wavelength of at least 600 nm, especially 600 to 700 nm. The radiation source may be, for example, a lamp fitted with a filter to pass light of wavelength longer than 600 nm. Suitable radiation sources and appropriate radiation dosages can be readily determined by those skilled in the art.

The invention is illustrated by the following Examples, in which pans are by weight unless indicated otherwise.

EXAMPLE 1

Palmitoyl oleoyl phosphatidylcholine is dissolved in diethyleneglycol monoethyl ether at a concentration of 0.25 g/ml. Samples of the solution obtained are used to dissolve varying amounts of zinc phthalocyanine (Zn Pc) by heating to 80° C. for 1 hour, followed by cooling for 3 hours while mixing. The mixtures obtained are centrifuged to remove undissolved zinc phthalocyanine. The volumes of the samples, amounts of Zn Pc mixed with the samples and concentrations of Zn Pc in the resulting solutions are shown in the following table:

| Volume of Sample (ml) | Amount of Zn Pc (mg) | Zn Pc Concentration in Resulting Solution (mg/ml) |
|---|---|---|
| 5.0 | 5.0 | 0.418 |
| 5.2 | 2.6 | 0.351 |
| 8.0 | 0.8 | 0.1 |

To the three resulting solutions, hydroxypropyl cellulose (15 mg per ml of solution) is added and the mixtures are heated at 80° C. to give, on cooling to ambient temperature, gels suitable for topical application in the treatment of psoriasis by photodynamic therapy.

EXAMPLE 2

Zinc phthalocyanine (ling) is added to diethylene glycol monoethyl ether (10 ml) and the mixture is heated to 80° C. for 1 hour, followed by cooling for 3 hours while mixing. The resulting mixture is centrifuged to remove undissolved zinc phthalocyanine. The solution obtained is mixed with hydroxypropyl cellulose (150 mg) and the mixture heated at 80° C. to give, on cooling, a gel suitable for topical administration in the treatment of psoriasis by photodynamic therapy.

EXAMPLE 3

Soya bean lecithin (phosphatidylcholine) is dissolved in diethyleneglycol monoethyl ether at a concentration of 0.25 g/ml. Samples of the solution obtained are used to dissolve varying amounts of zinc phthalocyanine by mixing at 80° C. for 1 hour, followed by cooling for 3 hours while mixing, the mixtures obtained being centrifuged to remove undissolved zinc phthalocyanine. The volumes of the solution samples, the amounts of Zn Pc mixed with the samples and the concentrations of Zn Pc in the resulting solutions are shown in the following table:

| Volume of Sample (ml) | Amount of Zn Pc (mg) | Zn Pc Concentration in Resulting Solution (mg/ml) |
|---|---|---|
| 5.2 | 5.2 | 0.436 |
| 5.4 | 2.7 | 0.374 |
| 11.0 | 1.1 | 0.1 |

The three resulting solutions are mixed with hydroxypropyl cellulose (15 mg per ml of solution) and the mixtures are heated at 80° C. to give, on cooling to ambient temperature, gels suitable for topical administration in the treatment of psoriasis by photodynamic therapy.

EXAMPLE 4

To a solution of α-tocopherol (1 g) in tert-butanol (100 ml) at 60° C. are added 95–100% pure palmitoyl oleoyl phosphatidyl choline (9 g) and 95–100% pure sodium dioleoyl phosphatidyl S-serine (1 g). When dissolution is complete, a solution of zinc phthalocyanine (100 mg) in N-methyl-2-pyrrolidone (3 ml), preheated to 60° C., is added. The resulting solution is mixed with an aqueous lactose solution (1.5 liters, containing 94.6 g/l α-D-lactose monohydrate and 270 mg/l sodium chloride, pH 4.1), using a dynamic mixer to form liposomes. The resulting dispersion is concentrated to 240 ml and dialysed against 2.4 liters of a 0.16 μm filtered lactose solution at 4° C. using a Filtron ultra-filtration unit, concentrated to 200 ml, dispensed into sterile vials and lyophilised using a Lyovac GT4 freeze drier. The liposomes are reconstituted when required by adding diethyleneglycol monoethyl ether (1 ml) to vials each containing lyophilised liposomes with a composition of palmitoyl phosphatidylcholine (27 mg), dioleoyl phosphatidylcholine (3 mg), zinc phthalocyanine (0.3 mg), lactose (94.6 mg) and sodium chloride (0.27 mg). After thorough mixing, the contents of the vials are centrifuged, when the insoluble lactose and sodium chloride form a pellet which is discarded. The resulting solution has a Zn Pc concentration of 0.3 mg/ml; this is mixed with hydroxypropyl cellulose (15 mg per ml of solution) and the mixture is heated to 80° C. to give, on cooling to ambient temperature, a gel suitable for topical administration in the treatment of psoriasis by photodynamic therapy.

EXAMPLE 5

Phosphatidylcholine is dissolved in diethylene glycol monoethyl ether at a concentration of 0.25 g/ml. Zinc phthalocyanine is dissolved in the solution as described in Example 3 to give a solution containing 75 µg/ml ZnPc. The solution is mixed with hydroxypropyl cellulose (15 mg per ml of solution) and the mixture is heated to 80° C. to give, on cooling to ambient temperature, a gel suitable for topical administration in the treatment of psoriasis by photodynamic therapy.

The performance of the gel in photodynamic therapy is tested on hairless mice having skin tape-stripped to simulate the condition of psoriatic skin. 25 µl samples of the gel are applied under a bandage to the right flanks of tape-stripped hairless mice. 25 µl samples of a placebo gel prepared by mixing the 0.25 g/ml solution of phosphatidylchloine in diethyleneglycol monoethyl ether with hydroxypropyl cellulose (15 mg per ml of solution) are applied under a bandage to the left flanks of the mice. After 24 hours, the bandages are removed and the skin fold thickness is measured and recorded as a percentage of the original skin fold thickness in the treated area. The areas treated with the gels are then irradiated with 120 J/cm² of filtered light having a wavelength of 610–690 nm. The change in skin fold thickness in the irradiated areas is measured at intervals over the next 4 days and recorded as a percentage of the original skin fold thickness. The results are shown below as the averages obtained from measurements on 6 animals.

% Change in Skin Fold Thickness

| Post-irradiation Time | % Change in Skin Fold Thickness | |
| --- | --- | --- |
| | Zn Pc Gel | Placebo Gel |
| 0 (before irradiation | 119.6 | 117.5 |
| 2 days | 151.6 | 97.8 |
| 3 days | 134.6 | 95.8 |
| 4 days | 126.4 | 110.3 |

EXAMPLE 6

Example 5 is repeated, but replacing the 100% diethyleneglycol ether carrier by a 1:1 mixture (by weight) of diethyleneglycol monoethyl ether and a polyethylene glycol having a molecular weight of 400, and dissolving ZnPc to give a solution containing 62.5 µg/ml ZnPc. The resulting gel is tested, along with a placebo gel which is identical except it does not contain ZnPc, as described in Example 5, except that 30 µl samples of the gels are applied to the flanks of the mice. The results are shown below as the averages obtained from measurements on 14 animals over 5 days post-irradiation.

% Change in Skin Fold Thickness

| Post-irradiation Time | % Change in Skin Fold Thickness | |
| --- | --- | --- |
| | ZnPc Gel | Placebo Gel |
| 0 (before irradiation) | 133 | 127.4 |
| 1 day | 178.2 | 121 |
| 2 days | 136.3 | 106.5 |
| 5 days | 108.6 | 102.1 |

I claim:

1. A topically administrable pharmaceutical composition comprising (A) zinc phthalocyanine, (B) as carrier for (A), (i) a monoalkyl ether of diethyleneglycol substantially in the absence of a N-alkylpyrrolidone, a N,N-dialkylbenzamide or dimethyl sulfoxide, or (ii) a mixture of a monoalkyl ether of diethyleneglycol with a lipid and (C) a gelling agent.

2. A composition according to claim 1, in which the monoalkyl ether is the ethyl ether of diethyleneglycol.

3. A composition according to claim 1, in which the carrier is a mixture of the monoalkyl ether of diethyleneglycol with a phospholipid.

4. A composition according to claim 3, in which the phospholipid is a synthetic phosphatidylcholine or a mixture thereof with a synthetic phosphatidylserine.

5. A composition according to claim 3, in which the phospholipid is a natural phosphatidylcholine.

6. A composition according to claim 3, in which the phospholipid is palmitoyl oleoyl phosphatidylcholine, soya bean phosphatidylcholine, or a mixture of palmitoyl oleoyl phosphatidylcholine and dioleoyl phosphatidylcholine.

7. A composition according to claim 1, in which the carrier (B) is a mixture of a monoalkyl ether of diethyleneglycol with liposomes in which the zinc phthalocyanine complex is entrapped.

8. A composition according to claim 7, in which the lipid component of the liposomes is a mixture of a neutral synthetic phospholipid with a charged synthetic phospholipid.

9. A composition according to claim 8, in which the synthetic phospholipid is a mixture of a phosphatidylcholine with a phosphatidylserine.

10. A composition according to claim 9, in which the synthetic phospholipid is a mixture of palmitoyl oleoyl phosphatidylcholine and dioleoyl phosphatidylserine.

11. A composition according to claim 9, in which the weight ratio of phosphatidylcholine to phosphatidylserine is from 60:40 to 95:5.

12. A composition according to claim 3, in which the phospholipid is present in an amount of up to 1 g per ml of the monoalkyl ether.

13. A composition according to claim 1, in which the zinc phthalocyanine (A) is present in an amount of 1–500 µg per ml of the carrier (B).

14. A composition according to claim 1, in which the gelling agent (C) is a cellulosic gel-forming polymer.

15. A composition according to claim 14, in which the gelling agent (C) is a hydroxyalkyl cellulose.

16. A composition according to claim 15, in which the gelling agent (C) is hydroxypropyl cellulose.

17. A composition according to claim 1, in which the gelling agent (C) is present in an amount of 0.1 to 10 parts by weight per 100 parts by volume of the composition.

18. A composition according to claim 1, which also contains a polyoxyalkylene glycol as diluent, in an amount up to 90% by volume of the composition.

19. A composition according to claim 18, in which the polyoxyalkylene glycol is a polyethylene glycol.

20. A method of photodynamic therapy for a hyperproliferative skin disease comprising applying topically to affected skin a composition according to claim 1 and irradiating the affected skin with visible radiation.

* * * * *